United States Patent
Govari et al.

(10) Patent No.: US 12,409,317 B2
(45) Date of Patent: Sep. 9, 2025

(54) BALLOON CATHETER WITH ULTRASONIC TRANSDUCERS

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 701 days.

(21) Appl. No.: 15/477,171

(22) Filed: Apr. 3, 2017

(65) Prior Publication Data
US 2018/0280658 A1 Oct. 4, 2018

(51) Int. Cl.
| A61M 25/00 | (2006.01) |
| A61B 5/00 | (2006.01) |
| A61B 5/06 | (2006.01) |
| A61B 5/287 | (2021.01) |
| A61B 8/00 | (2006.01) |
| A61B 8/08 | (2006.01) |
| A61B 8/12 | (2006.01) |
| A61M 25/10 | (2013.01) |

(Continued)

(52) U.S. Cl.
CPC .............. *A61N 1/05* (2013.01); *A61B 5/063* (2013.01); *A61B 5/287* (2021.01); *A61B 5/6853* (2013.01); *A61B 8/0883* (2013.01); *A61B 8/12* (2013.01); *A61B 8/4254* (2013.01); *A61B 8/445* (2013.01); *A61N 1/04* (2013.01); *A61B 5/1076* (2013.01); *A61B 5/6886* (2013.01); *A61B 18/1492* (2013.01); *A61M 2025/1075* (2013.01)

(58) Field of Classification Search
CPC ...................................................... A61B 8/445
See application file for complete search history.

(56) References Cited

U.S. PATENT DOCUMENTS

| 4,917,097 A | 4/1990 | Proudian et al. |
| 5,391,199 A | 2/1995 | Ben-Haim |

(Continued)

FOREIGN PATENT DOCUMENTS

| CN | 103784195 A | 5/2014 |
| WO | WO 88/09150 A1 | 12/1988 |

(Continued)

OTHER PUBLICATIONS

European Search Report dated Aug. 7, 2018, EP Application No. 18165387.4.

(Continued)

*Primary Examiner* — Amal Aly Farag
(74) *Attorney, Agent, or Firm* — Etan S. Chatlynne; Calderon Safran & Wright P.C.

(57) ABSTRACT

A balloon catheter that has one or more ultrasonic transducers to map a body cavity and to measure thicknesses of walls in the body cavity during an ablation procedure. The balloon of the catheter is deployable through a lumen into the body cavity with a flexible printed circuit board that has a first side attached to the exterior wall of the inflatable balloon and a second side opposite the first side. There is also provided an ultrasonic transducer mounted on the first side of the flexible printed circuit board and encapsulated between the exterior wall of the balloon and the flexible printed circuit board. A method of making or using the balloon catheter is also provided.

12 Claims, 5 Drawing Sheets

(51) Int. Cl.
  *A61N 1/04*   (2006.01)
  *A61N 1/05*   (2006.01)
  *A61B 5/107*   (2006.01)
  *A61B 18/14*   (2006.01)

(56) References Cited

U.S. PATENT DOCUMENTS

| | | | |
|---|---|---|---|
| 5,443,489 | A | 8/1995 | Ben-Haim |
| 5,558,091 | A | 9/1996 | Acker et al. |
| 5,722,972 | A | 3/1998 | Power et al. |
| 5,865,801 | A | 2/1999 | Houser |
| 5,944,022 | A | 8/1999 | Nardella et al. |
| 5,971,955 | A | 10/1999 | Nap et al. |
| 5,983,126 | A | 11/1999 | Wittkampf |
| 6,172,499 | B1 | 1/2001 | Ashe |
| 6,177,792 | B1 | 1/2001 | Govari et al. |
| 6,456,864 | B1 | 9/2002 | Swanson et al. |
| 6,514,249 | B1* | 2/2003 | Maguire ............... A61B 18/00 606/37 |
| 6,690,963 | B2 | 2/2004 | Ben-Haim et al. |
| 6,788,967 | B2 | 9/2004 | Ben-Haim et al. |
| 7,101,368 | B2* | 9/2006 | Lafontaine ............. A61B 18/02 606/21 |
| 8,819,928 | B2 | 9/2014 | Nix et al. |
| 2004/0249401 | A1 | 12/2004 | Rabiner et al. |
| 2008/0243214 | A1* | 10/2008 | Koblish ............... A61B 5/0422 600/374 |
| 2012/0265188 | A1* | 10/2012 | Buchbinder ............ A61F 7/123 606/21 |
| 2014/0276789 | A1 | 9/2014 | Dandler et al. |
| 2015/0025532 | A1* | 1/2015 | Hanson .............. A61B 18/1492 606/41 |
| 2015/0366508 | A1* | 12/2015 | Chou ................... A61B 8/4477 600/374 |
| 2016/0051321 | A1* | 2/2016 | Salahieh ............ A61B 1/00082 600/439 |
| 2018/0146948 | A1* | 5/2018 | Chou ...................... A61B 8/12 |

FOREIGN PATENT DOCUMENTS

| | | |
|---|---|---|
| WO | WO 93/04727 A1 | 3/1993 |
| WO | WO 2016/183285 A1 | 11/2016 |

OTHER PUBLICATIONS

National Intellectual Property Administration, P.R. China, First Office Action, date of issue Jul. 20, 2022, translated to English, 15 pages.

* cited by examiner

BALLOON CATHETER WITH ULTRASONIC TRANSDUCERS

FIELD OF THE INVENTION

The present invention relates generally to invasive medical probes, and specifically to a balloon catheter comprising one or more ultrasonic transducers.

BACKGROUND OF THE INVENTION

A balloon catheter comprises an inflatable balloon at its distal end that can be inflated and deflated as necessary. In operation, the balloon is typically deflated while the catheter is inserted into a body cavity (e.g., a heart) of a patient, inflated in order to perform the necessary procedure, and deflated again upon completing the procedure.

U.S. Pat. No. 5,865,801 to Houser, whose disclosure is incorporated herein by reference, describes a catheter with a dilatation balloon fixed to the catheter tubing near its distal end. The catheter may include piezoelectric ultrasonic transducers on the balloon's exterior surface allowing a physician to utilize ultrasound to position the catheter and to view a surface surrounding the catheter.

U.S. Pat. No. 8,819,928 to Nix et al., whose disclosure is incorporated herein by reference, describes an ultrasonic imaging catheter. The catheter includes a flexible circuit electrically coupled to a transducer array mounted on a distal end of the catheter, and a balloon at the distal end close to the transducer array. The catheter includes a stent mounted on the balloon, the stent carrying one or more drugs designed to be eluted or washed into a patient's blood stream after the stent has been inserted into a target area within the patient's vascular system.

International Patent WO 88/09150 to Griffith et al., whose disclosure is incorporated herein by reference, describes an ultrasonic imaging array and balloon catheter assembly. The catheter includes an array of miniature ultrasound crystals that are mounted on a preassembled subassembly, which is, in turn, mounted on a small lumen catheter that provides dimensional and other quantitative information relating to arterial wall geometry and character at disease or obstruction sites. Balloons are also mounted on the catheter to make it possible to use the catheter for an angioplasty procedure.

U.S. Pat. No. 5,722,972 to Power et al., whose disclosure is incorporated herein by reference, describes an excimer laser catheter that can be used for ablation of atherosclerotic blockage. The catheter includes a tube-like basic body with a distal end and a proximal end, at least two balloon members positioned at the distal end, and ultrasonic probe positioned between two of the balloon members. The ultrasonic probe includes a series of piezo crystals and at least one multiplexer which can activate the piezo crystals in a phased manner.

International patent WO 93/04727 to McNicholas et al., whose disclosure is incorporated herein by reference, describes a balloon catheter that can be used to treat body tissue. The catheter includes a balloon and means for ultrasonically viewing prostatic tissue.

U.S. Pat. No. 4,917,097 to Proudian et al., whose disclosure is incorporated herein by reference, describes an in vivo imaging device that is configured to image small body cavities.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a medical apparatus, including a probe having a distal end configured for insertion into a body cavity and containing a lumen that opens through the distal end, an inflatable balloon deployable through the lumen into the body cavity, the balloon having an exterior wall, a flexible printed circuit board having a first side attached to the exterior wall of the inflatable balloon and a second side opposite the first side, and an ultrasonic transducer mounted on the first side of the flexible printed circuit board and encapsulated between the exterior wall of the balloon and the flexible printed circuit board.

In some embodiments, the ultrasonic transducer includes a piezo ceramic crystal. In additional embodiments, the ultrasonic transducer is configured to operate in amplitude mode. In further embodiments, the ultrasonic transducer is configured to generate a signal between one and ten megahertz in order to determine a distance between the ultrasonic transducer and tissue in the body cavity. In supplemental embodiments, the ultrasonic transducer can be configured to generate a signal greater than twenty megahertz in order to determine a thickness of tissue in contact with the second side of the flexible circuit board.

In some embodiments, the medical apparatus may include an electrode mounted on the second side of the flexible circuit board and configured as a location sensor. In additional embodiments wherein the medical apparatus include the electrode, the medical apparatus may include a processor configured to generate a map of the body cavity based on a distance between the ultrasonic transducer and tissue in the body cavity and a signal from the electrode. In further embodiments, the body cavity includes a chamber of a heart.

There is also provided, in accordance with an embodiment of the present invention, a method, including providing a probe having a distal end configured for insertion into a body cavity and containing a lumen that opens through the distal end, providing an inflatable balloon deployable through the lumen into the body cavity, the balloon having an exterior wall, attaching a first side of a flexible printed circuit board to the exterior wall of the inflatable balloon, the flexible circuit board having a second side opposite the first side, and mounting an ultrasonic transducer on the first side of the flexible printed circuit board, thereby encapsulating the ultrasonic transducer between the exterior wall of the balloon and the flexible printed circuit board.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Balloon catheters can be configured to perform invasive procedures such as intracardiac ablation and anatomical mapping. While performing intracardiac ablation, balloon catheters can typically ablate larger areas of tissue than traditional single tip catheters that perform point-by-point ablation. Furthermore, balloon catheters can ablate the larger areas of tissue at a single time, reducing procedure time and exposure to radiation related to the use of fluoroscopy during the procedure.

During an anatomical mapping procedure, a map is created that comprises map points collected from the balloon catheter. Each map point comprises a respective coordinate within a body cavity, and while mapping a body cavity such as a chamber of a heart, the map points may be registered to a pre-acquired image of the body cavity, thereby providing a practical visualization of the body cavity.

In embodiments of the present invention, a balloon catheter comprises one or more ultrasonic transducers that can be used to map a body cavity, and to measure thicknesses of walls in the body cavity during an ablation procedure. As described hereinbelow, the balloon catheter comprises a distal end configured for insertion into a body cavity and containing a lumen that opens through the distal end. The balloon catheter also comprises an inflatable balloon deployable through the lumen into the body cavity, the balloon having an exterior wall, and a flexible printed circuit board having a first side attached to the exterior wall of the inflatable balloon and a second side opposite the first side. The balloon catheter additionally comprises an ultrasonic transducer mounted on the first side of the flexible printed circuit board and encapsulated between the exterior wall of the balloon and the flexible printed circuit board.

While inserted into a body cavity (e.g., a heart), the ultrasonic transducers can transmit and receive a high frequency signal, and analyze the signal in order to determine a current distance between the ultrasonic transducers and a wall of the body cavity. As a medical professional maneuvers the distal end within the body cavity and collects distances between the distal end and walls of the body cavity, the distances can be used to generate a map of the body cavity. Additionally, when the distal end of the balloon catheter is in contact with tissue in the body cavity (e.g., during an ablation procedure), the high frequency signal can be analyzed to determine a thickness of the tissue.

In some embodiments, each given ultrasonic transducer may comprise a piezo ceramic crystal, which is typically brittle. Encapsulating the ultrasonic transducers between the exterior wall of the balloon and the flexible printed circuit board can help protect and prevent the ultrasonic transducers from breaking when the distal end of the balloon catheter is in contact with tissue in the body cavity.

System Description

Figure 1:
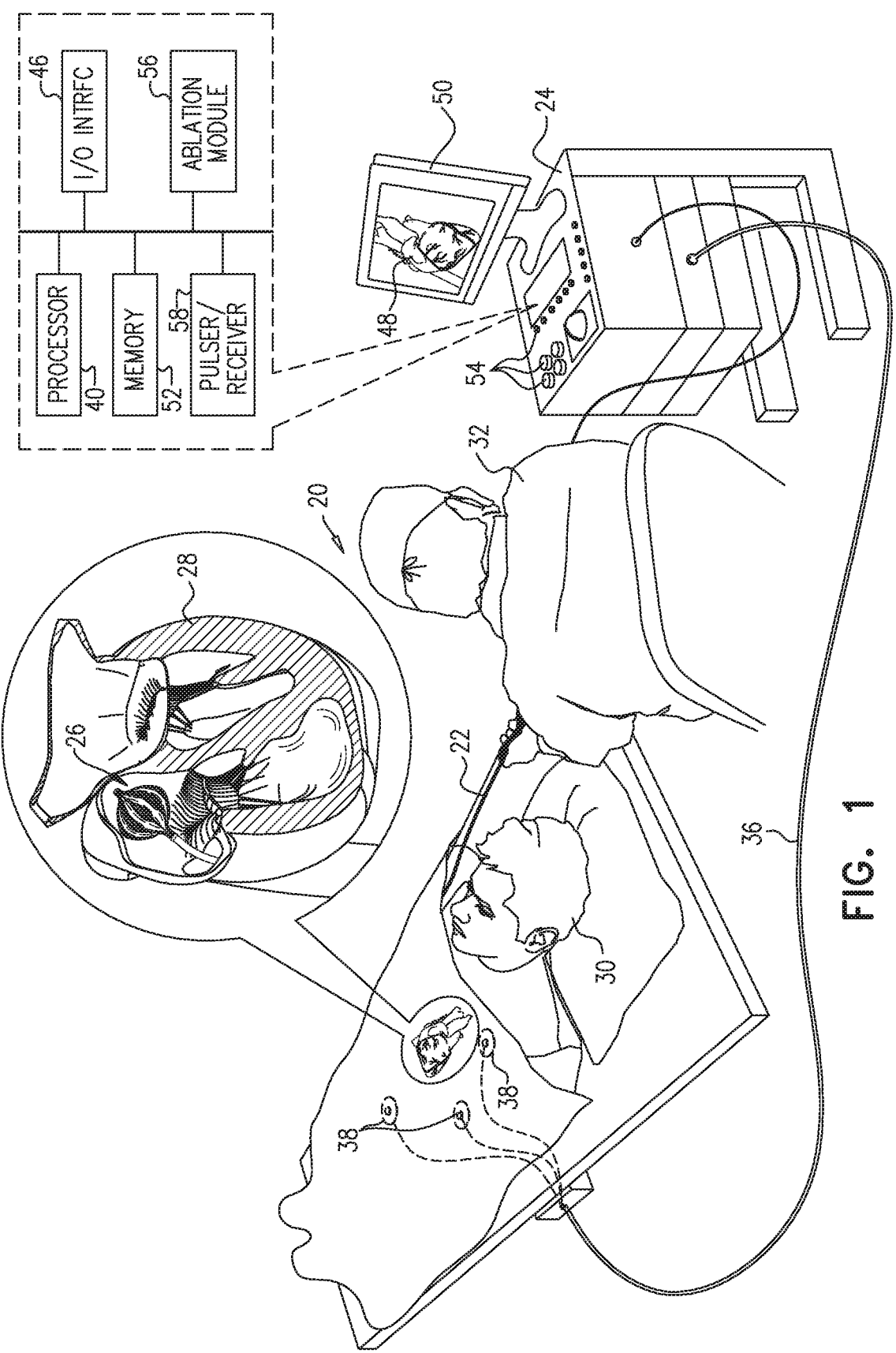
FIG. 1 is a schematic, pictorial illustration of a medical system comprising a balloon catheter with a distal end, in accordance with an embodiment of the present invention.
Figure 2:
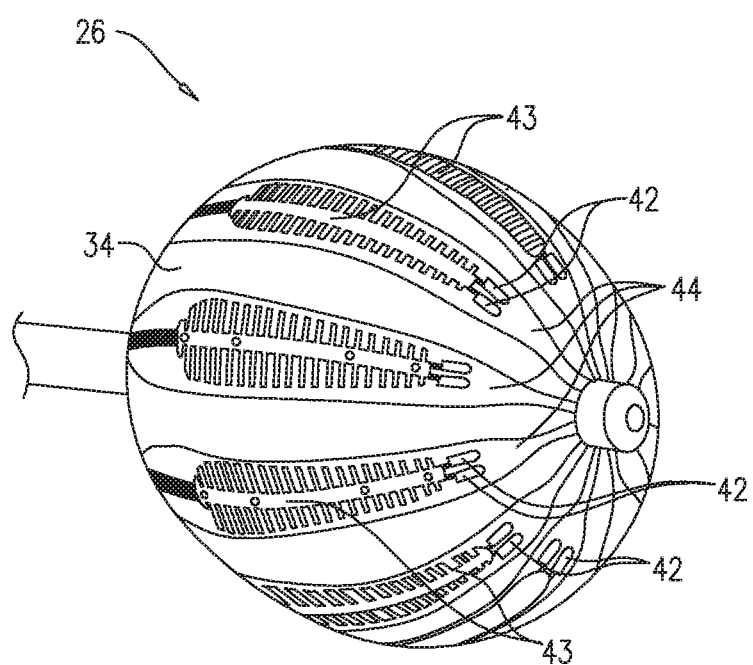
FIG. 2 is a schematic pictorial illustration of the distal end comprising multiple flexible printed circuit boards affixed to a balloon, in accordance with an embodiment of the present invention.

FIG. 1 is a schematic, pictorial illustration of a medical system 20 comprising a medical probe 22 and a control console 24, and FIG. 2 is a schematic pictorial illustration of a distal end 26 of the medical probe, in accordance with an embodiment of the present invention. System 20 may be based, for example, on the CARTO® system, produced by Biosense Webster Inc. (Diamond Bar, California, U.S.A.). In embodiments described hereinbelow, medical probe 22 comprises a balloon catheter that is used for diagnostic or therapeutic treatment, such as for mapping electrical potentials and/or for performing ablation procedures in a heart 28 of a patient 30. Alternatively, probe 22 may be used, mutatis mutandis, for other therapeutic and/or diagnostic purposes in the heart or in other body organs.

During a medical procedure, a medical professional 32 inserts medical probe 22 into a biocompatible sheath (not shown) that has been pre-positioned in a lumen of the patient so that a balloon 34 (FIG. 2) affixed to distal end 26 of the medical probe enters the lumen (e.g., a chamber of heart 28). Balloon 34 is typically formed from bio-compatible material such as polyethylene terephthalate (PET), polyurethane, nylon, or silicone.

Console 24 is connected, by a cable 36, to body surface electrodes, which typically comprise adhesive skin patches 38 that are affixed to patient 30. Console 24 comprises a processor 40 that determines position coordinates of distal end 26 inside heart 28 based on impedances measured between adhesive skin patches 38 and one or more electrodes 42 (also referred to as microelectrodes 42) that are mounted on a flexible circuit board 44 that is affixed to balloon 34. In the configuration shown in FIG. 2, distal end 26 comprises multiple flexible circuit boards 44 affixed to balloon 34, each of the circuit boards comprising a pair of microelectrodes 42.

Processor 40 typically comprises a general-purpose computer, with suitable front end and interface circuits for receiving signals from elements of probe 22 (e.g., microelectrodes 42) and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

Although the medical system shown in FIG. 1 uses impedance-based sensing to measure a location of distal end 26, other position tracking techniques may be used (e.g., techniques using magnetic-based sensors). Impedance-based position tracking techniques are described, for example, in U.S. Pat. Nos. 5,983,126, 6,456,864 and 5,944,022, whose disclosures are incorporated herein by reference. Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. The method of position sensing described hereinabove is implemented in the above-mentioned CARTO™ system and is described in detail in the patents cited above.

Console 24 also comprises an input/output (I/O) communications interface 46 that enables console 24 to transfer signals from, and/or transfer signals to electrodes 42 in probe 22 and adhesive skin patches 38. In embodiments described hereinbelow, processor 40 can use signals received from microelectrodes 42 and adhesive skin patches 38 to generate a map 48 that shows the position of balloon 34 in the patient's body. During the procedure, processor 40 can present map 48 to medical professional 32 on a display 50, and store data representing the map in a memory 52. Memory 52 may comprise any suitable volatile and/or non-volatile memory, such as random access memory or a hard disk drive. In some embodiments, medical professional 32 can manipulate map 48 using one or more input devices 54.

As shown in FIG. 2, distal end 26 comprises multiple flexible circuit boards 44 mounted on balloon 34, each of the flexible circuit boards comprising a pair of microelectrodes 42, and an electrode 43 (also referred to herein as an ablation electrode 43) that can be used to ablate cardiac tissue in heart 28. Flexible circuit board 44 comprises an insulated substrate, typically implemented with polyimide, and electrodes 42 and 43 typically comprise gold overlaying the substrate.

Control console 24 also comprises an ablation module 56 and a pulser/receiver circuit 58. Control console 24 is configured to monitor and control ablation parameters such as the level and the duration of ablation power applied to the ablation electrodes. Pulser/receiver circuit 58 may be based, for example, on JSR Ultrasonics' DPR-300 Pulser/Receiver, produced by Imaginant (Pittsford, NY, U.S.A.), and the functionality of pulser/receiver circuit 58 is described hereinbelow.

Figure 3:
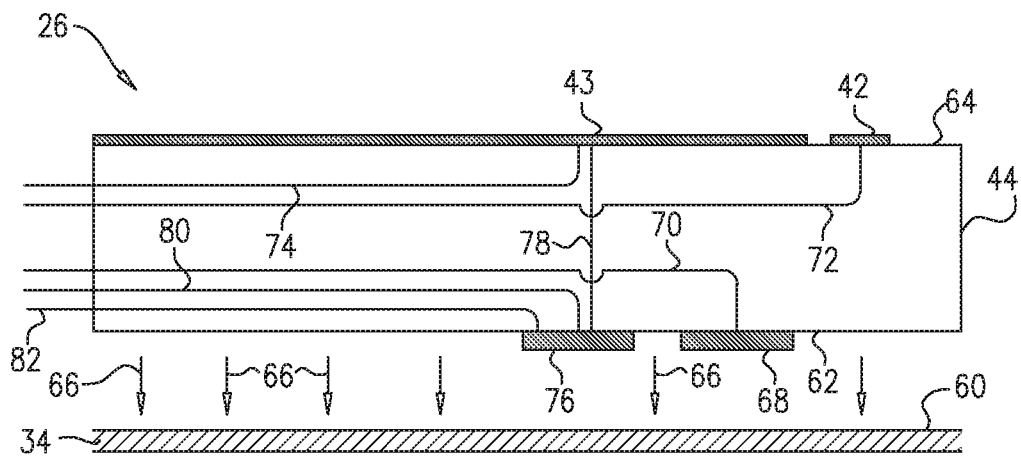
FIG. 3 is a schematic exploded view showing an ultrasonic transducer mounted on a given flexible circuit board, in accordance with an embodiment of the present invention.

FIG. 3 is a schematic side view of a portion of distal end 26, showing components of the distal end, in accordance with an embodiment of the present invention. Balloon 34 comprises an exterior wall 60, and flexible circuit board 44 has a first side and a second side 64 opposite the first side. Each given microelectrode 42 is coupled, by a conductor 72, to circuitry (including processor 40) in control console 24 that enables processor 40 to determine a location of the given microelectrode, and each ablation electrode 43 is coupled to ablation module 56 by a conductor 74.

In embodiments of the present invention, an ultrasonic transducer 68 is mounted on first side 62 of the flexible circuit board, electrodes 42 and 43 are mounted on second side 64, and the first side is then attached to exterior wall 60, as indicated by arrows 66. Ultrasonic transducer 68 is coupled to pulser/receiver circuit 58 by a connection 70, and may comprise a piezo ceramic crystal, such as lead zirconate titanate (PZT), lead titanate (PT), or lead metaniobate (PbNb$_2$O$_6$).

In operation, medical system 20 typically operates in amplitude mode (also known as A-mode). While operating in A-mode, pulser/receiver circuit 58 conveys a first electrical signal to ultrasonic transducer that excites the piezo ceramic crystal, and as a result of exciting the piezo ceramic crystal, ultrasonic transducer 68 transmits a unidirectional high frequency signal that travels as a relatively narrow beam.

While distal end 26 is positioned into a body cavity such as heart 28, the high frequency signal will bounce (i.e., reflect) off of surfaces in patient 30. Upon returning to ultrasonic transducer 68, the reflected signal deforms the piezo ceramic crystal, causing the piezo ceramic crystal to generate a second electrical signal that is conveyed to pulser/receiver circuit 58. Processor 40 can then measure the time between the first and the second electrical signals in order to determine a distance between ultrasonic transducer 68 and the respective surfaces. As described in the description referencing FIG. 5 hereinbelow, surfaces that can reflect the high frequency signal when distal end is inserted into heart 28 may include second side 64 and tissue in the body cavity.

In the configuration shown in FIG. 3, electrodes 42 and 43 are mounted on second side 64 of flexible circuit board 44. While embodiments described herein have microelectrodes 42 configured as location sensors, configuring the microelectrodes to perform other tasks during a medical procedure is considered to be within the spirit and scope of the present invention. For example, some or all of microelectrodes 42 may be configured to measure electrical activity of heart 28. Additionally or alternatively, ablation electrodes 43 may also be configured as location sensors (i.e., in addition to or instead of being configured to ablate tissue).

In some embodiments, flexible circuit board 44 may comprise a thermocouple 76 mounted on first side 62. Thermocouple 76 may be coupled to ablation electrode 43 by a conductive via 78, and the thermocouple may be formed as a junction between a copper conductor 80 and a constantan conductor 82. Conductors 80 and 82 are typically connected to ablation module 56 and enable the module to monitor the temperature of ablation electrode 43 during an ablation procedure. Conductors 70, 72, 74, 80 and 82 can be formed as conducting lines embedded in the substrate of flexible circuit board 44.

Figure 4:
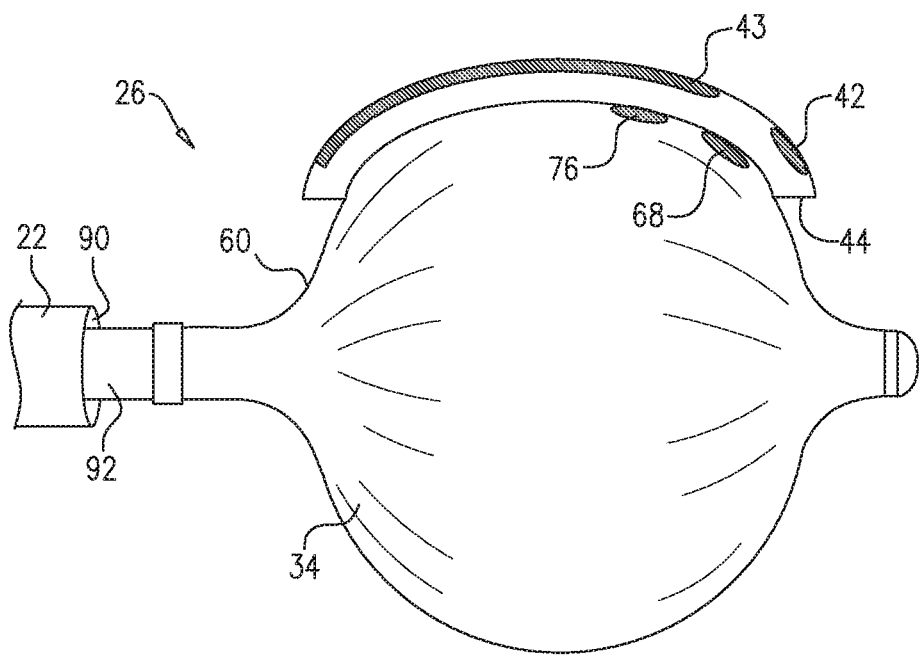
FIG. 4 is a schematic view of the distal end of the balloon catheter when the balloon is inflated, in accordance with an embodiment of the present invention.

FIG. 4 is a schematic side view of distal end 26 when balloon 34 is inflated, in accordance with an embodiment of the present invention. Balloon 34 is affixed to a tubular shaft 92 that is configured to extend from a lumen 90 at a distal end of medical probe 22, and balloon 34 is configured to be deployed through the lumen into a body cavity such as heart 28. As shown in FIG. 4, and thermocouple 76 are ultrasonic transducer 68 encapsulated between exterior wall 60 of the balloon and first side 62 (see first side 62 and transducer 68 in FIG. 3) of flexible printed circuit board 44.

Figure 5B:
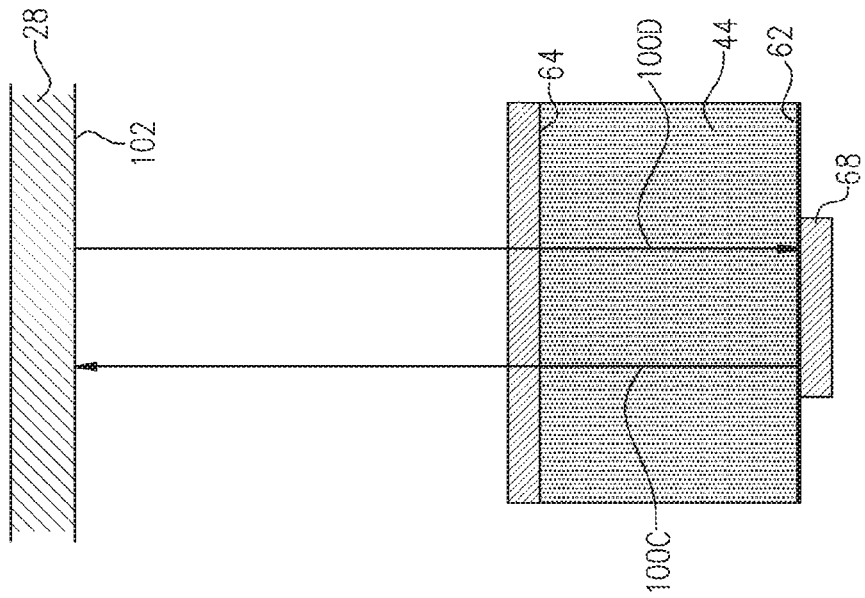
FIGS. 5A and 5B are schematic illustrations of high frequency signals that are generated by the ultrasonic transducer, in accordance with an embodiment of the present invention.
Figure 5A:
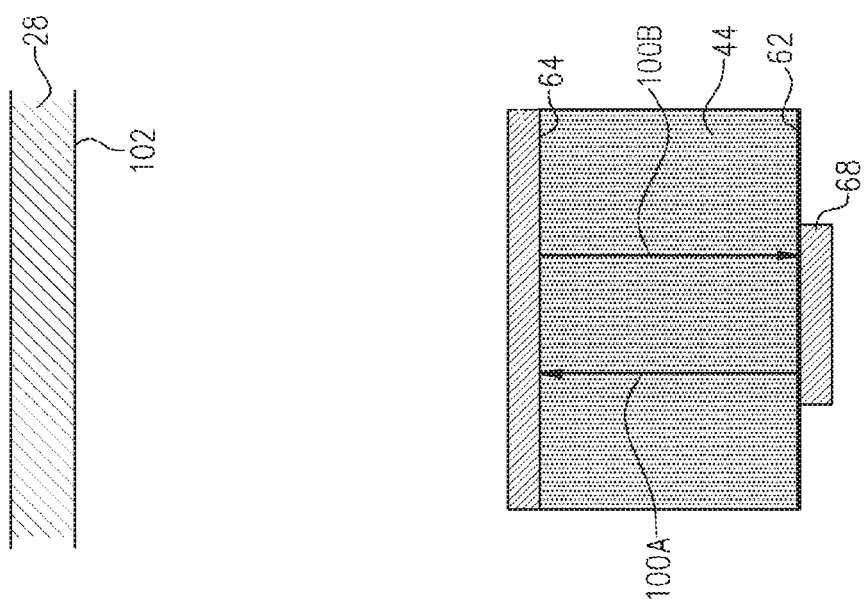

FIGS. 5A and 5B, referred to collectively as FIG. 5, are schematic illustrations of high frequency signals that are generated by ultrasonic transducer 68, in accordance with an embodiment of the present invention. Pulser/receiver circuit 58 conveys a high frequency electrical pulse to transducer 68, which then transmits a high frequency signal of pulsed ultrasound from transducer 68 when it operates in the A-mode. As explained below the high frequency ultrasound signal travels along a signal path, and the signal separates into a number of different signals of pulsed ultrasound having the same frequency but reduced amplitude compared with the original signal. The reduced amplitude signals travel along respective associated signal paths.

In the example shown in FIG. 5, the different signals and their associated signal paths are generically termed signals and paths 100. The signals and their associated paths are differentiated herein by appending a letter to the identifying numeral, so that different signals have associated signal paths 100A-100D.

Thus, as shown in FIG. 5A, on receipt of the electrical pulse from circuit 58, ultrasonic transducer 68 transmits an initial high frequency ultrasound signal, and the signal travels through flexible circuit board 44 along a signal path 100A until it strikes an interface formed by electrode 43 contacting second side 64. At the interface, i.e. at second side 64, a portion of the initial signal reflects as a first high frequency signal, which travels back to the ultrasonic transducer along a path 100B.

As shown in FIG. 5B, the remainder of signal transmits through the interface at side 64, as a high frequency signal which travels along a path 100C. Signal continues traveling along path 100C until it strikes the surface of endocardial tissue 102 in heart 28, at which point it reflects as a high frequency signal which travels along a path 100D back to the ultrasonic transducer.

While for clarity the paths of the signals have been separated in FIG. 5, it will be understood that the paths may actually be substantially collinear, for example in the case that the paths are normal to transducer 68 and side 64. Nonetheless, the paths are separate in time.

From a knowledge of the times of transmittal of signal from transducer 68, and of receipt of signal at the transducer, pulser/receiver circuit 58 is able to evaluate the "time of flight" of the ultrasound signal generated by the transducer, and provides the value of the time of flight to processor 40. Processor 40 uses the time of flight, and known values of the speed of sound in the media in which the ultrasound pulse travels, as well as the thicknesses of board 44 and electrode 43, to evaluate the distance between transducer 68 and tissue 102. As described herein, the processor may use the distances from different transducers 68 to tissue 102 to generate a map of the body cavity containing distal end 26.

Figures 6, 7:
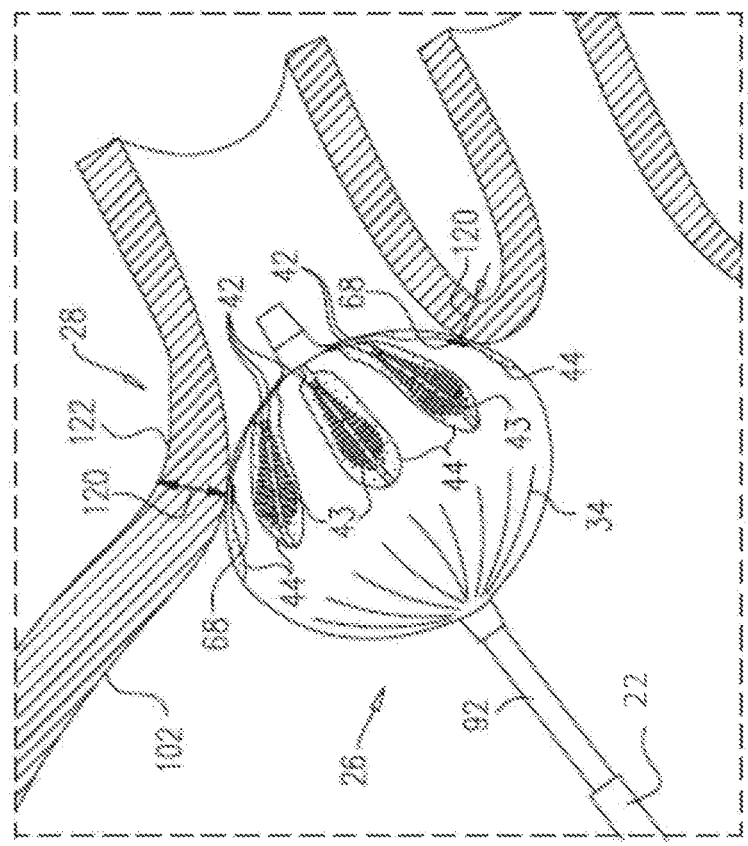
FIG. 6 is a schematic view of the distal end of the catheter positioned within a cardiac chamber, in accordance with an embodiment of the present invention.
FIG. 7 is a schematic view of the distal end of the catheter in contact with a wall of the cardiac chamber, in accordance with an embodiment of the present invention.

FIGS. 6 and 7 are schematic detail views of distal end 26 in a chamber of heart 28, in accordance with an embodiment of the present invention. In FIG. 6, balloon 34 is inflated and deployed through lumen 90 (see FIG. 4) but does not contact endocardial tissue 102, and in FIG. 7, the balloon is pressed against endocardial tissue 102 in heart 28 so that one or more electrodes 43 are in contact with the endocardial tissue.

As shown in FIG. 6, while balloon 34 is positioned in a body cavity such as a chamber of heart 28, but not in contact with endocardial tissue 102, processor 40 can use location measurements from microelectrodes 42 to generate a three-dimensional software model that represents balloon 34 and locations of ultrasonic transducers 68. As medical professional 32 maneuvers distal end 26 within the cardiac chamber, ultrasonic transducers 68 can transmit and receive first high frequency signals (typically at frequencies between 1-10 megahertz), and generated in response to corresponding electrical signals from pulser/receiver circuit 58) that enable processor 40 to determine distances 110 between ultrasonic transducers 68 and endocardial tissue 102. Processor 40 can use the locations of ultrasonic transducers 68 (i.e., determined by the three-dimensional model) and distances 110 to construct map 48.

In FIG. 7, ablation electrodes 43 are in contact with endocardial tissue 102 (e.g., while the ablation electrodes are performing an ablation procedure). In this situation circuit 58 is configured to convey second high frequency electrical signals (typically at frequencies greater than 20 megahertz) to ultrasonic transducers 68, which in turn transmit and receive second high frequency ultrasound signals that enable processor 40 to determine distances 120 between the ultrasonic transducers and epicardial tissue 122. Distances 120 indicate thicknesses at various locations on the wall of heart 28.

In operation, the second higher frequency signals used to determine distances 120 have a higher resolution and a shorter range that the first high frequency signals used to determine distances 110. Additionally, processor 40 can be configured to use different calculation factors when determining distances 110 and 120, since the high frequency signals typically travel at different speeds in different media (i.e., blood in FIG. 6, and tissue in FIG. 7).

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising: a probe having a distal end configured for insertion into a body cavity of an organ and containing a lumen that opens through the distal end;
   an inflatable balloon deployable through the lumen into the body cavity, the balloon having an exterior wall;
   a flexible printed circuit board having a first side attached to the exterior wall of the inflatable balloon and a second side opposite the first side, the second side spaced apart from the first side, the flexible printed circuit board having an ablation electrode and a pair of micro-electrodes disposed on the second side of the flexible printed circuit board and configured to measure electrical activity of the organ;
   (1) a thermocouple coupled to the ablation electrode by a conductive via; and
   (2) an ultrasonic transducer mounted on the first side of the flexible printed circuit board and disposed between the exterior wall of the balloon and the flexible printed circuit board;
   wherein when the balloon is deployed into the body cavity the micro-electrodes provide location signals of the balloon location and the ultrasonic transducer location.

2. The medical apparatus according to claim 1, wherein the ultrasonic transducer comprises a piezo ceramic crystal.

3. The medical apparatus according to claim 1, wherein the ultrasonic transducer is configured to operate in amplitude mode.

4. The medical apparatus according to claim 1, wherein the ultrasonic transducer is configured to generate a signal between one and ten megahertz in order to determine a distance between the ultrasonic transducer and tissue in the body cavity.

5. The medical apparatus according to claim 1, and further comprising a processor configured to generate a map of the body cavity based on a distance between the ultrasonic transducer and tissue in the body cavity and the location signals from the micro-electrodes.

6. The medical apparatus according to claim 5, wherein the body cavity comprises a chamber of a heart.

7. A method, comprising:
   providing a probe having a distal end configured for insertion into a heart and containing a lumen that opens through the distal end;
   providing an inflatable balloon deployable through the lumen into the body cavity, the balloon having an exterior wall;
   attaching a first side of a flexible printed circuit board to the exterior wall of the inflatable balloon, the flexible circuit board having a second side opposite the first side, the second side spaced apart from the first side, the flexible printed circuit board having an ablation electrode and a pair of micro-electrodes on the second side;
   coupling a thermocouple mounted on the first side of the flexible printed circuit board to the ablation electrode mounted on the second side by a conductive via, thereby disposing the thermocouple between the exterior wall of the balloon and the flexible printed circuit board; and mounting an ultrasonic transducer on the first side of the flexible printed circuit board, thereby disposing the ultrasonic transducer between the exterior wall of the balloon and the flexible printed circuit board;

wherein when the balloon is deployed into the body cavity the micro-electrodes provide location signals of the balloon location and the ultrasonic transducer location.

8. The method according to claim 7, wherein the ultrasonic transducer comprises a piezo ceramic crystal.

9. The method according to claim 7 and comprising operating the ultrasonic transducer in amplitude mode.

10. The method according to claim 7, and comprising generating, by the ultrasonic transducer, a signal between one and ten megahertz, and determining, by a processor based on the signal, a distance between the ultrasonic transducer and tissue in the body cavity.

11. The medical apparatus according to claim 10, and further comprising generating, by the processor, a map of the body cavity based on the distance between the ultrasonic transducer and tissue in the heart and the location signals from the pair of micro-electrodes.

12. The method according to claim 7, and comprising generating, by the ultrasonic transducer, a signal, and determining by a processor based on the signal, a thickness of tissue in contact with the second side of the flexible circuit board.

* * * * *